United States Patent
Gelman et al.

(10) Patent No.: US 10,818,126 B2
(45) Date of Patent: *Oct. 27, 2020

(54) APPARATUS FOR PARI-MUTUEL RACING GAME WITH FINISH ORDER BETTING

(71) Applicant: CFPH, LLC, New York, NY (US)

(72) Inventors: Geoffrey M. Gelman, Brooklyn, NY (US); Dean P. Alderucci, Westport, CT (US)

(73) Assignee: CFPH, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/414,884

(22) Filed: May 17, 2019

(65) Prior Publication Data

US 2019/0304239 A1    Oct. 3, 2019

Related U.S. Application Data

(63) Continuation of application No. 15/593,907, filed on May 12, 2017, now Pat. No. 10,325,443, which is a continuation of application No. 11/868,673, filed on Oct. 8, 2007, now Pat. No. 9,652,926.

(60) Provisional application No. 60/828,516, filed on Oct. 6, 2006.

(51) Int. Cl.
| | |
|---|---|
| *G07F 17/32* | (2006.01) |
| *G01G 17/08* | (2006.01) |
| *G01G 19/414* | (2006.01) |
| *A61B 5/103* | (2006.01) |

(52) U.S. Cl.
CPC ............. *G07F 17/32* (2013.01); *G01G 17/08* (2013.01); *G01G 19/414* (2013.01); *G07F 17/3248* (2013.01); *G07F 17/3288* (2013.01); *A61B 5/1038* (2013.01)

(58) Field of Classification Search
CPC ..... A61B 5/1036; A61B 5/1038; G07F 17/32; G07F 17/3248; G07F 17/3288; G01G 17/08; G01G 19/44; G01G 19/414
See application file for complete search history.

(56) References Cited

U.S. PATENT DOCUMENTS

| | | |
|---|---|---|
| 3,169,022 A | 2/1965 | Kretsinger |
| 3,616,690 A | 11/1971 | Harden |
| 4,014,398 A | 3/1977 | Gresko |
| 4,823,894 A | 4/1989 | Koerner |
| 5,411,258 A | 5/1995 | Wilson et al. |
| 5,511,571 A | 4/1996 | Adrezin |
| 5,842,921 A | 12/1998 | Mindes et al. |
| 5,957,775 A | 9/1999 | Cherry |
| 6,210,275 B1 | 4/2001 | Olsen |
| 6,309,307 B1 | 10/2001 | Krause et al. |
| 6,386,538 B1 | 5/2002 | Mejia |
| 6,437,257 B1 | 8/2002 | Yoshida |
| 6,576,849 B2 | 6/2003 | Bliss |

(Continued)

FOREIGN PATENT DOCUMENTS

| | | |
|---|---|---|
| JP | 2001-243394 | 9/2001 |
| JP | 2005-004552 | 1/2005 |

OTHER PUBLICATIONS

Australian Exam Report for Application No. 2007303065, dated Aug. 2, 2010 (3 pages).

(Continued)

*Primary Examiner* — Randy W Gibson

(57) ABSTRACT

In various embodiments, a device may test the health of race participants in order to ensure the fairness of a bet on an order of finish.

14 Claims, 8 Drawing Sheets

(56) References Cited

U.S. PATENT DOCUMENTS

| | | |
|---|---|---|
| 6,592,454 B2 | 7/2003 | Libby et al. |
| 6,820,033 B1 | 11/2004 | Hapgood |
| 6,860,806 B2 | 3/2005 | Kojima et al. |
| 7,094,151 B2 | 8/2006 | Downes |
| 7,100,439 B2 | 9/2006 | Carlucci |
| 7,107,832 B2 | 9/2006 | Blumentritt |
| 8,131,498 B1 | 3/2012 | McCauley |
| 9,652,926 B2 | 5/2017 | Gelman et al. |
| 10,325,443 B2 | 6/2019 | Gelman et al. |
| 2002/0065120 A1 | 5/2002 | Lee |
| 2003/0199315 A1 | 10/2003 | Downes P.E. |
| 2004/0229671 A1 | 11/2004 | Stronach et al. |
| 2004/0229675 A1 | 11/2004 | Cannella |
| 2004/0235542 A1 | 11/2004 | Stonach et al. |
| 2005/0003888 A1 | 1/2005 | Asher et al. |
| 2005/0116410 A1 | 6/2005 | Vlazny et al. |
| 2005/0181868 A1 | 8/2005 | Vlazny et al. |
| 2005/0282610 A1 | 12/2005 | Palmer et al. |
| 2005/0288081 A1 | 12/2005 | Amaitis et al. |
| 2006/0009279 A1 | 1/2006 | Amaitis et al. |
| 2006/0135252 A1 | 6/2006 | Amaitis et al. |
| 2006/0246983 A1 | 11/2006 | Huard et al. |
| 2008/0167580 A1 | 7/2008 | Avni |
| 2013/0346021 A1 | 12/2013 | Stevens |

OTHER PUBLICATIONS

New Zealand Exam Report for Application No. 576008, dated Sep. 28, 2010 (2 pages).

810

| Gate | Horse | Odds |
|---|---|---|
| 1 | Whiz Tail | 33:2 |
| 2 | Dasher | 7:2 |
| 3 | Zippy | 3:1 |
| 4 | High Tide | 6:1 |
| 5 | Sir Henry | 9:2 |
| 6 | Splotchy | 27:1 |
| 7 | Big Foot | 2:1 |
| 8 | Whiskers | 55:1 |

} 815

Current Finish Required for Reverse Bet

APPARATUS FOR PARI-MUTUEL RACING GAME WITH FINISH ORDER BETTING

This application is a continuation of U.S. patent application Ser. No. 15/593,907 filed May 12, 2017 which is a continuation of U.S. patent application Ser. No. 11/868,673 filed Oct. 8, 2007 (now U.S. Pat. No. 9,652,926) which claims priority to U.S. Provisional Application Ser. No. 60/828,516, filed Oct. 6, 2006, all of which are incorporated by reference herein in their entireties:

BACKGROUND

Racing games have, at times, enjoyed some popularity. Some games allow pari-mutuel betting.

SUMMARY

In various embodiments, a person may bet on the order in which racing participants may finish.

BRIEF DESCRIPTION OF THE DRAWINGS

FIG. 8 shows a display according to some embodiments.

DETAILED DESCRIPTION

In various embodiments, bettors at a race, such as at a horse race, may bet that participants in the race will finish in a particular order. One particular order may represent a "least likely" order, or reverse order, such that participants finish exactly opposite to the way payoff odds from a pari-mutuel system would predict. For example, the particular order may have the horse which is favored to win finishing last, the horse which is the next most favored finishing second to last, and so on. A bet on such a finish in reverse order may be termed a "reverse bet" herein.

In various embodiments it may be very unlikely that participants in a race finish in reverse order, especially if there are a significant number of participants, such as eight, or twelve participants. Thus, large payouts may be offered for a bet made on a reverse order finish.

In various embodiments, with the potential for large payouts may come the potential for manipulation. A horse that is favored to win a race may turn out to be slightly injured. A person with inside knowledge of the horse's condition could make a bet on the reverse finish, knowing that the favored horse will likely finish last, and thereby making the reverse finish far more likely.

Figure 1:
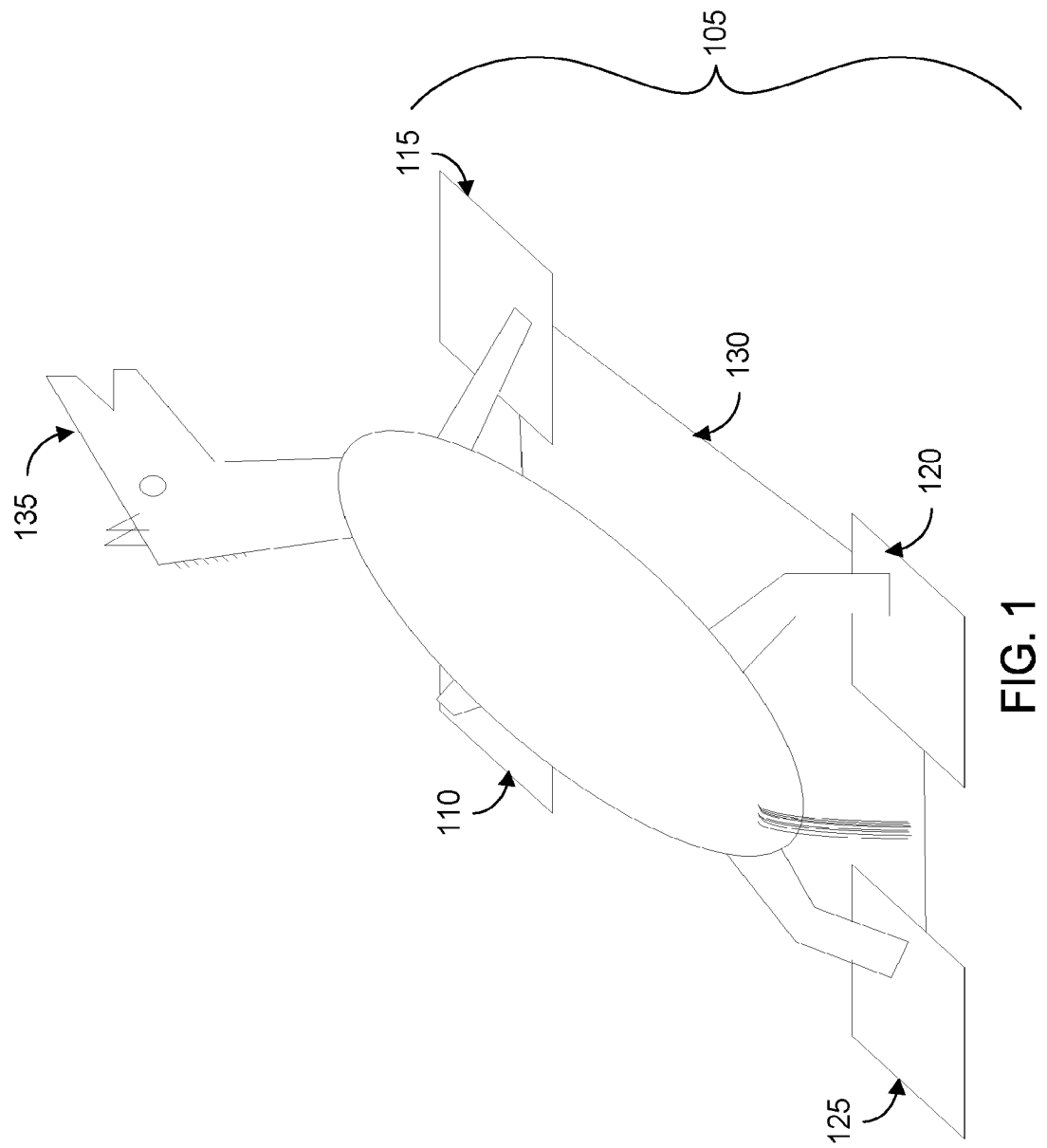
FIG. 1 shows a scale according to some embodiments.
Figure 2:
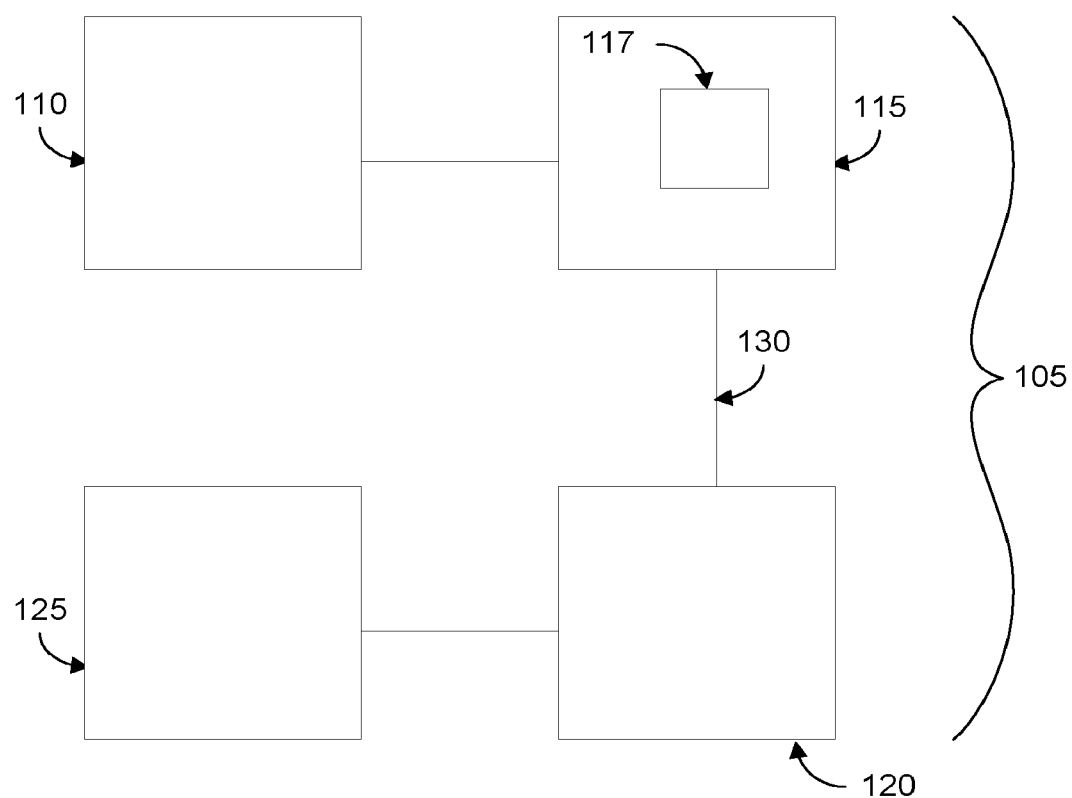
FIG. 2 shows a schematic diagram of a scale according to some embodiments.

According to some embodiments, a specialized scale is used to test a horse for injuries. FIG. 1 shows a scale 105 according to some embodiments. Four weighing units, 110, 115, 120, and 125 may each separately take a weight measurement. The units may be configured so that a horse (e.g., horse 135) may have one leg on each unit. The units may be linked by cables or wires (e.g., cable 130) or may communicate wirelessly. A schematic diagram of the scale 105 is shown in FIG. 2.

Figure 3:
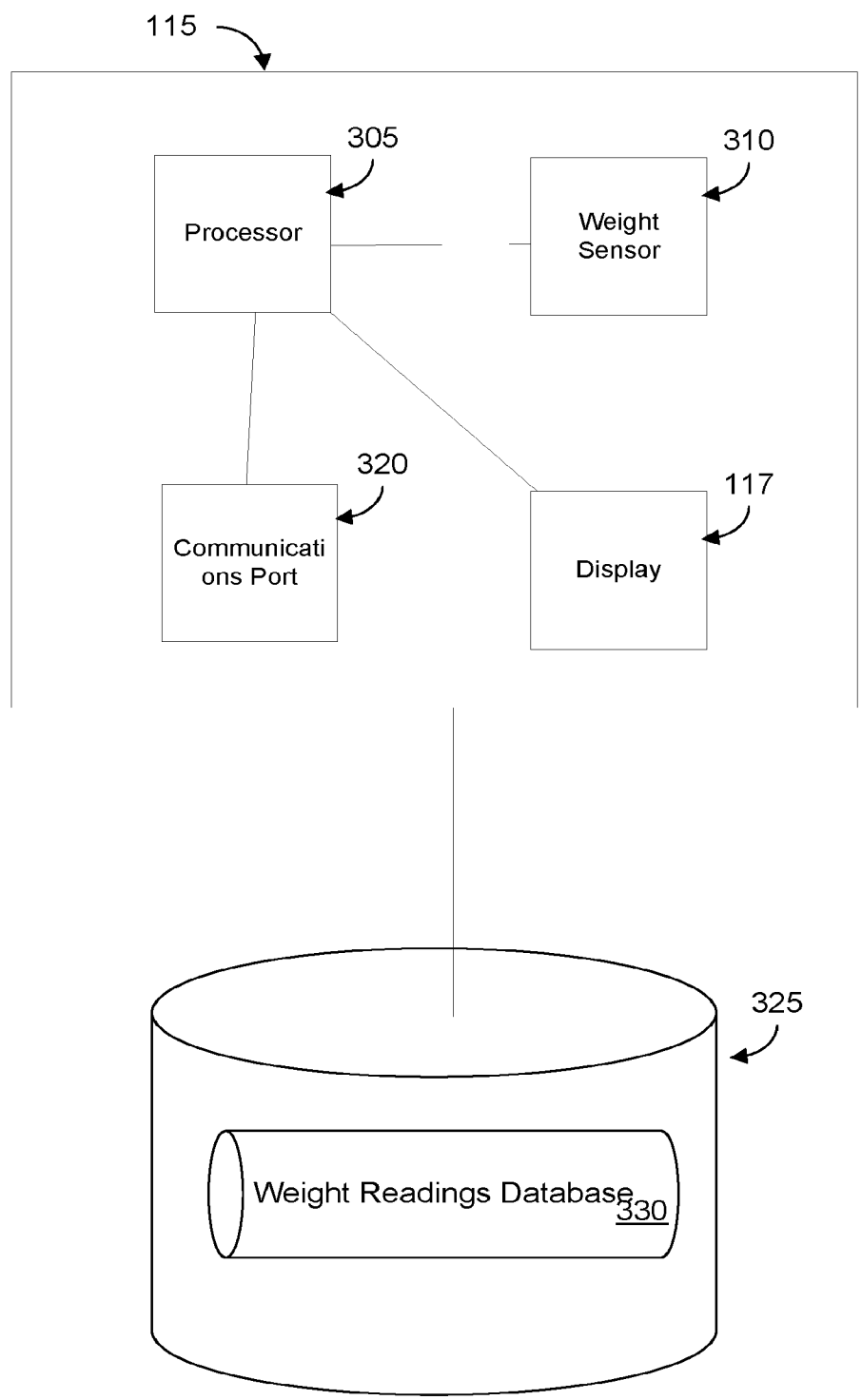
FIG. 3 shows a schematic diagram of a component of a scale according to some embodiments.

In operation, a horse 135 may stand with one leg on each unit. Weight readings may thereupon be taken at each unit. The horse may be kept on the scale 105 for some period of time (e.g., for one minute), so that weight readings may be taken as a function of time. Weight readings may be analyzed at one of the units (e.g., at unit 115). FIG. 3 depicts a schematic diagram of unit 115. Unit 115 may include a storage device 325 with a weight readings database 330 for storing weight readings gathered from the four units. Unit 115 may further include a communications port 320, which may receive communications from other units, which may send instructions or other communications to other units, and/or which may communicate with other devices. Unit 115 may include a weight sensor 310. Other units may also include such a sensor. The weight sensor may sense the weight of the horse on the unit. Unit 115 may include a processor for interpreting weight readings. Display 315 may provide an indication of weight or an indication other messages, such as indications of whether or not the horse is fit.

In various embodiments, the scale 105 seeks to determine if the horse is favoring one or more legs with its weight. A horse that has a leg injury may tend to put less weight on the injured leg than it does on other legs. The scale may compare weight readings from the two front units (e.g., 110 and 115). The scale may compare weight readings from the two back units. The scale may compare two weight readings from any other units. If weight readings from two units being compared diverge by more than a predetermined weight (e.g., 40 pounds), then processor 305 may determine that the horse is injured. In some embodiments, if weight readings differ by more than a predetermined percentage (e.g., by more than 10%), then processor 305 may determine that the horse is injured. Based on determinations made by the processor, display 315 may display a message. The message may read, for example, "horse is fit," or "horse is injured." The display may also show actual weight readings, percentage differences in weight readings, and so on.

In various embodiments, it may be anticipated that the horse will naturally shift his weight back and forth. Thus, weight readings may be captured over time. The weight readings may then be averaged together to arrive at an average reading at one of the units. For example, a given unit may take weight readings once per second for 60 seconds. The unit may then average the weight readings to determine an average weight placed by the horse on that unit. Thus, even if the horse is shifting his weight from leg to leg, the units may be able to capture an average weight reading that represents the weight a horse would put on a given leg if it were standing completely still.

Reverse Bet

Figure 4:
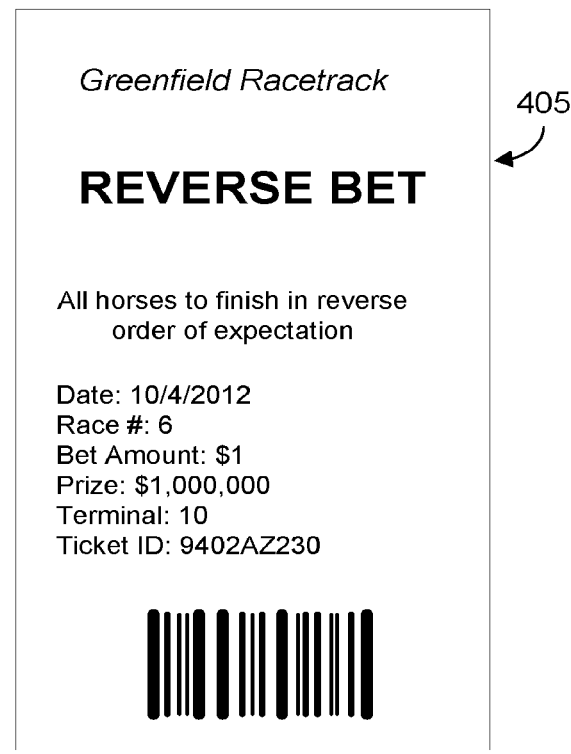
FIG. 4 shows a ticket according to some embodiments.

FIG. 4 shows a ticket, receipt, betting slip, or other indication or representation of a bet that has been made by a bettor. The ticket 405 includes a name of the racetrack, (e.g., "Greenfield Racetrack"), an indication of the type of bet (e.g., "Reverse Bet"), an explanation of the bet, a date the bet was made, a race on which the bet was made, an amount of the bet, a potential prize for the bet, a betting terminal at which the bet was made, an identifier for the ticket, and a bar code. It will be appreciated that not all items of information depicted on the ticket 405 may be shown, or that additional items may be shown. The ticket 405 may allow the player to claim his prize in the event that the bet is successful (e.g., in the event that horses in race 6 do finish in the reverse order of expectation). If the bet is successful, the player may bring the ticket to a desk at a race track, or may insert it into a betting terminal, kiosk, or other device.

Figure 5:
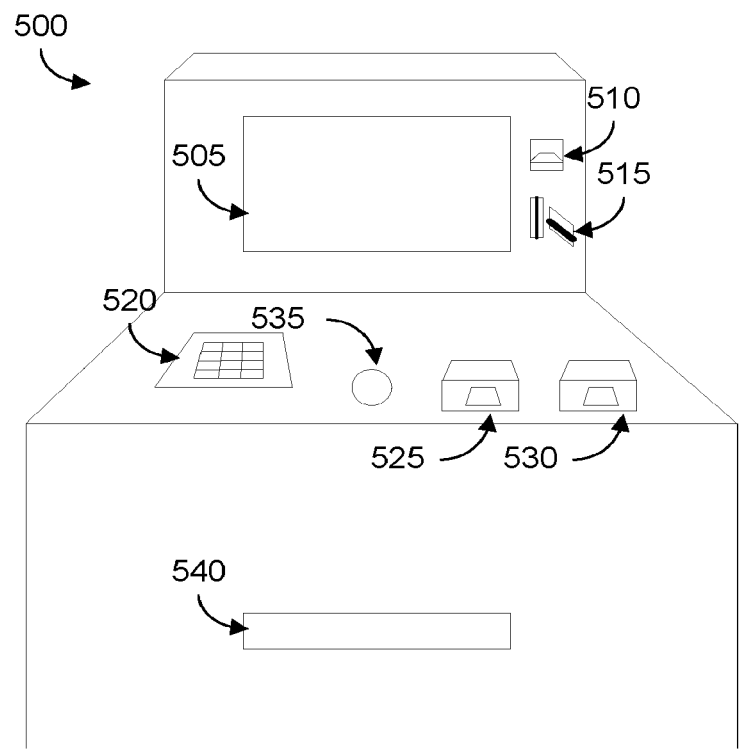
FIG. 5 shows a betting apparatus according to some embodiments.

FIG. 5 shows a betting terminal 500 according to some embodiments. The betting terminal may allow a player to place bets on one or more races. Such bets may include bets on a horse to win a race, bets on all horses in a race to finish in reverse order of expectation, or any other bets. The terminal may also allow other transactions, such allowing a player to claim winnings from a successful bet. The terminal may include a display 505, a cash acceptor 510, a card acceptor (e.g., a credit card acceptor, e.g., a debit card acceptor, e.g., an acceptor of an identification card for a player), a keypad 520 or other input device, a ticket printer 525, ticket reader 530, a trackball or other input device 535, and a cash dispenser 540. As will be appreciated, a betting terminal may take many other configurations.

Figure 6:
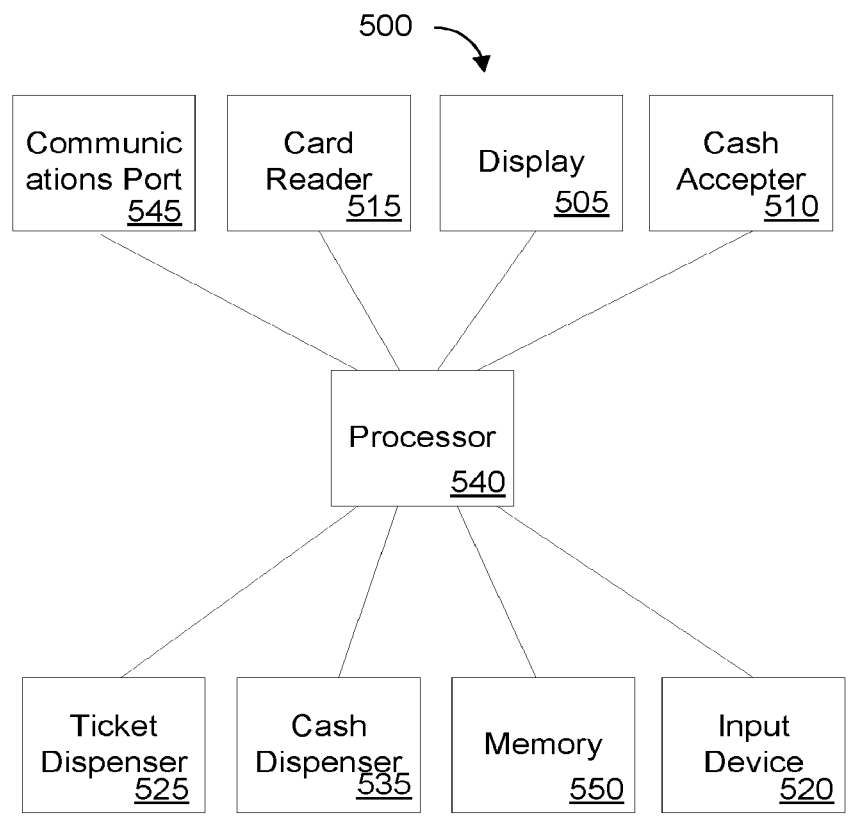
FIG. 6 shows a schematic diagram of a betting apparatus according to some embodiments.

FIG. 6 shows a schematic representation of a betting terminal 500 according to some embodiments.

Figure 7:
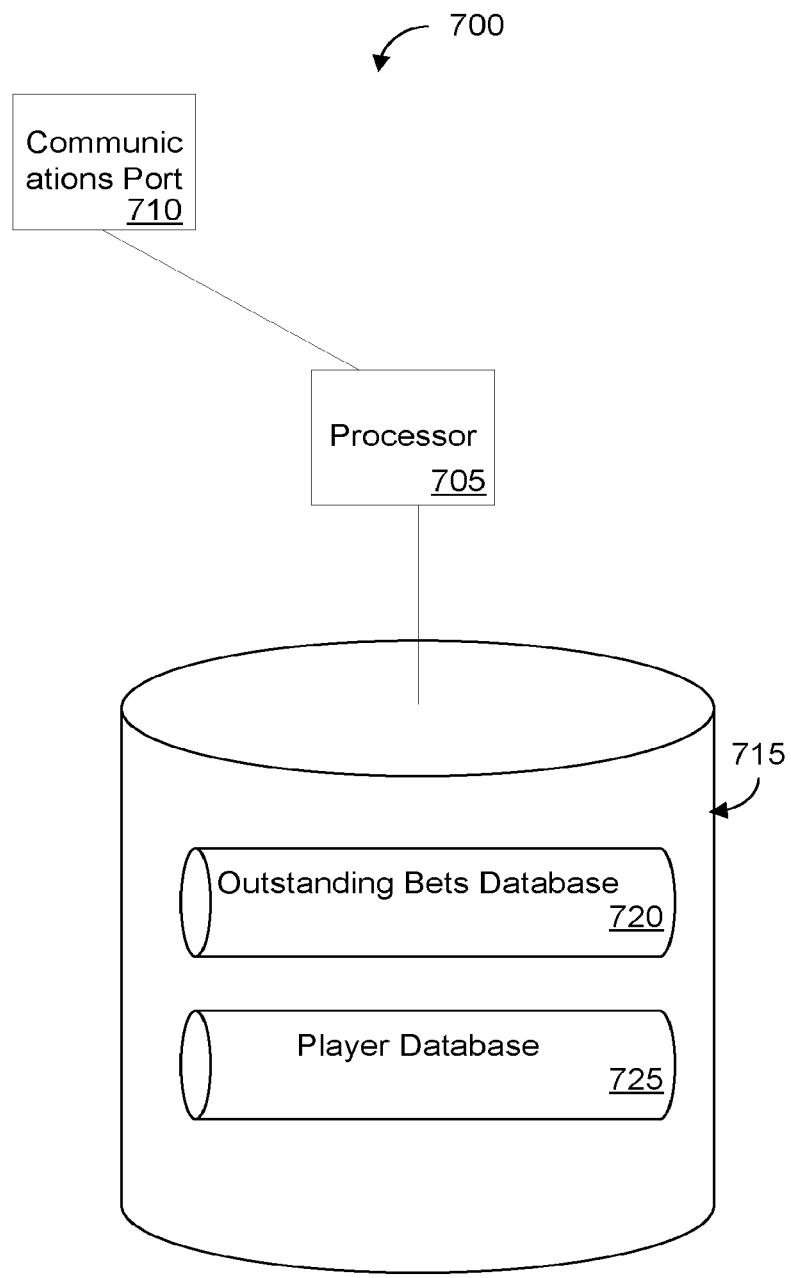
FIG. 7 shows a schematic diagram of server according to some embodiments.

FIG. 7 shows a schematic representation of a server 700, according to some embodiments. The server may receive (e.g., via the communications port 710) indications of bets that have been made at betting terminals, such as at betting terminals located throughout a racetrack. The server may keep track of outstanding bets, e.g., using a memory 715 with an outstanding bets database 720. From the outstanding bets, the server may be able to compute (e.g., using processor 705) odds on various horses, payouts due to particular players, and the order of finish that would be winning for a reverse bet. The player database 725 may allow the server to track the betting histories of players, to allow the server to verify an identifying document presented by a player in conjunction with a winning ticket, or to perform any other function.

The server 700 may supply data for a public display 810 (shown in FIG. 8), such a tote board. The data presented may include gate numbers or horse numbers for a particular race (e.g., for the next scheduled race), horse names, and current payoff odds for someone betting on a given horse to win. As shown in FIG. 8, for example, the horse named "Whiz Tail" is scheduled to start the next race out of gate 1. A player who has bet 2 on Whiz Tail stands to win 33 should Whiz Tail win the race.

FIG. 8 also shows an indication 820 of the current order of finish that would be required for the reverse bet to pay. As shown in the figure, the horses must finish in the following gate order: #8, #6, #1, #4, #5, #2, #3, and #7 for the reverse bet to pay. This order corresponds, in this case, to the least favored horse winning the race (i.e., the horse with the highest payoff odds), the next least favorite horse finishing second, and so on.

In some embodiments, various bettors may continue to place bets on one or more of the horses to win. Betting may continue until some cutoff time, such as five minutes before the race is scheduled to start. As more bets are placed, the payoff odds may change, since the payoff odds may depend on what bets have been placed in a pari-mutuel system. Thus, the finish order required for the reverse bet to pay may also change.

In various embodiments, a person who places a reverse bet may win his bet if the horses finish in the reverse order of expectation at the time he places his bet. Thus, even if the expected order of finish changes later, the person may still win if the reverse order of expected finish occurs based on when he made his bet. In some embodiments, a person who makes a reverse bet only wins if the horses finish in the reverse order of expectation for the moment in time when betting closes.

In various embodiments, more or less information may be displayed on the display 810.

The following sections I-X provide a guide to interpreting the present application.

I. Determining

The term "determining" and grammatical variants thereof (e.g., to determine a price, determining a value, determine an object which meets a certain criterion) is used in an extremely broad sense. The term "determining" encompasses a wide variety of actions and therefore "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing, and the like.

The term "determining" does not imply certainty or absolute precision, and therefore "determining" can include estimating, extrapolating, predicting, guessing and the like.

The term "determining" does not imply that mathematical processing must be performed, and does not imply that numerical methods must be used, and does not imply that an algorithm or process is used.

The term "determining" does not imply that any particular device must be used. For example, a computer need not necessarily perform the determining.

II. Forms of Sentences

Where a limitation of a first claim would cover one of a feature as well as more than one of a feature (e.g., a limitation such as "at least one widget" covers one widget as well as more than one widget), and where in a second claim that depends on the first claim, the second claim uses a definite article "the" to refer to the limitation (e.g., "the widget"), this does not imply that the first claim covers only one of the feature, and this does not imply that the second claim covers only one of the feature (e.g., "the widget" can cover both one widget and more than one widget).

When an ordinal number (such as "fire, " "second", "third" and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

When a single device, article or other product is described herein, more than one device/article (whether or not they cooperate) may alternatively be used in place of the single device/article that is described. Accordingly, the functionality that is described as being possessed by a device may alternatively be possessed by more than one device/article (whether or not they cooperate).

Similarly, where more than one device, article or other product is described herein (whether or not they cooperate), a single device/article may alternatively be used in place of the more than one device or article that is described. For example, a plurality of computer-based devices may be substituted with a single computer-based device. Accordingly, the various functionality that is described as being possessed by more than one device or article may alternatively be possessed by a single device/article.

The functionality and/or the features of a single device that is described may be alternatively embodied by one or more other devices which are described but are not explicitly described as having such functionality/features. Thus, other embodiments need not include the described device itself, but rather can include the one or more other devices which would, in those other embodiments, have such functionality/features.

III. Terms

The term "product" means any machine, manufacture and/or composition of matter, unless expressly specified otherwise.

The term "process" means any process, algorithm, method or the like, unless expressly specified otherwise.

Each process (whether called a method, algorithm or otherwise) inherently includes one or more steps, and therefore all references to a "step" or "steps" of a process have an inherent antecedent basis in the mere recitation of the term 'process' or a like term. Accordingly, any reference in a claim to a 'step' or 'steps' of a process has sufficient antecedent basis.

The term "invention" and the like mean "the one or more inventions disclosed in this application", unless expressly specified otherwise.

The terms "an embodiment", "embodiment", "embodiments", "the embodiment", "the embodiments", "one or more embodiments", "some embodiments", "certain embodiments", "one embodiment", "another embodiment" and the like mean "one or more (but not all) embodiments of the disclosed invention(s)", unless expressly specified otherwise.

The term "variation" of an invention means an embodiment of the invention, unless expressly specified otherwise.

A reference to "another embodiment" in describing an embodiment does not imply that the referenced embodiment is mutually exclusive with another embodiment (e.g., an embodiment described before the referenced embodiment), unless expressly specified otherwise.

The terms "including", "comprising" and variations thereof mean "including but not limited to", unless expressly specified otherwise.

The terms "a", "an" and "the" mean "one or more", unless expressly specified otherwise.

The term "plurality" means "two or more", unless expressly specified otherwise.

The term "herein" means "in the present application, including anything which may be incorporated by reference", unless expressly specified otherwise.

The phrase "at least one of", when such phrase modifies a plurality of things (such as an enumerated list of things) means any combination of one or more of those things, unless expressly specified otherwise. For example, the phrase "at least one of a widget, a car and a wheel" means either (i) a widget, (ii) a car, (iii) a wheel, (iv) a widget and a car, (v) a widget and a wheel, (vi) a car and a wheel, or (vii) a widget, a car and a wheel. The phrase "at least one of", when such phrase modifies a plurality of things does not mean "one of" each of the plurality of things.

Numerical terms such as "one", "two", etc. when used as cardinal numbers to indicate quantity of something (e.g., one widget, two widgets), mean the quantity indicated by that numerical term, but do not mean at least the quantity indicated by that numerical term. For example, the phrase "one widget" does not mean "at least one widget", and therefore the phrase "one widget" does not cover, e.g., two widgets.

The phrase "based on" does not mean "based only on", unless expressly specified otherwise. In other words, the phrase "based on" describes both "based only on" and "based at least on". The phrase "based at least on" is equivalent to the phrase "based at least in part on".

The term "represent" and like terms are not exclusive, unless expressly specified otherwise. For example, the term "represents" do not mean "represents only", unless expressly specified otherwise. In other words, the phrase "the data represents a credit card number" describes both "the data represents only a credit card number" and "the data represents a credit card number and the data also represents something else".

The term "whereby" is used herein only to precede a clause or other set of words that express only the intended result, objective or consequence of something that is previously and explicitly recited. Thus, when the term "whereby" is used in a claim, the clause or other words that the term "whereby" modifies do not establish specific further limitations of the claim or otherwise restricts the meaning or scope of the claim.

The term "e.g." and like terms mean "for example", and thus does not limit the term or phrase it explains. For example, in the sentence "the computer sends data (e.g., instructions, a data structure) over the Internet", the term "e.g." explains that "instructions" are an example of "data" that the computer may send over the Internet, and also explains that "a data structure" is an example of "data" that the computer may send over the Internet. However, both "instructions" and "a data structure" are merely examples of "data", and other things besides "instructions" and "a data structure" can be "data".

The term "respective" and like terms mean "taken individually". Thus if two or more things have "respective" characteristics, then each such thing has its own characteristic, and these characteristics can be different from each other but need not be. For example, the phrase "each of two machines has a respective function" means that the first such machine has a function and the second such machine has a function as well. The function of the first machine may or may not be the same as the function of the second machine.

The term "i.e." and like terms mean "that is", and thus limits the term or phrase it explains. For example, in the sentence "the computer sends data (i.e., instructions) over the Internet", the term "i.e." explains that "instructions" are the "data" that the computer sends over the Internet.

Any given numerical range shall include whole and fractions of numbers within the range. For example, the range "1 to 10" shall be interpreted to specifically include whole numbers between 1 and 10 (e.g., 1, 2, 3, 4, . . . 9) and non-whole numbers (e.g., 1.1, 1.2, . . . 1.9).

Where two or more terms or phrases are synonymous (e.g., because of an explicit statement that the terms or phrases are synonymous), instances of one such term/phrase does not mean instances of another such term/phrase must have a different meaning. For example, where a statement renders the meaning of "including" to be synonymous with "including but not limited to", the mere usage of the phrase "including but not limited to" does not mean that the term "including" means something other than "including but not limited to".

IV. Disclosed Examples and Terminology Are Not Limiting

Neither the Title (set forth at the beginning of the first page of the present application) nor the Abstract (set forth at the end of the present application) is to be taken as limiting in any way as the scope of the disclosed invention(s). An Abstract has been included in this application merely because an Abstract of not more than 150 words is required under 37 C.F.R. § 1.72(b).

The title of the present application and headings of sections provided in the present application are for convenience only, and are not to be taken as limiting the disclosure in any way.

Numerous embodiments are described in the present application, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

No embodiment of method steps or product elements described in the present application constitutes the invention claimed herein, or is essential to the invention claimed herein, or is coextensive with the invention claimed herein, except where it is either expressly stated to be so in this specification or expressly recited in a claim.

The preambles of the claims that follow recite purposes, benefits and possible uses of the claimed invention only and do not limit the claimed invention.

The present disclosure is not a literal description of all embodiments of the invention(s). Also, the present disclosure is not a listing of features of the invention(s) which must be present in all embodiments.

Devices that are described as in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for long period of time (e.g. weeks at a time). In addition, devices that are in communication with each other may communicate directly or indirectly through one or more intermediaries.

A description of an embodiment with several components or features does not imply that all or even any of such components/features are required. On the contrary, a variety of optional components are described to illustrate the wide variety of possible embodiments of the present invention(s). Unless otherwise specified explicitly, no component/feature is essential or required.

Although process steps, algorithms or the like may be described or claimed in a particular sequential order, such processes may be configured to work in different orders. In other words, any sequence or order of steps that may be explicitly described or claimed does not necessarily indicate a requirement that the steps be performed in that order. The steps of processes described herein may be performed in any order possible. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention(s), and does not imply that the illustrated process is preferred.

Although a process may be described as including a plurality of steps, that does not imply that all or any of the steps are preferred, essential or required. Various other embodiments within the scope of the described invention(s) include other processes that omit some or all of the described steps. Unless otherwise specified explicitly, no step is essential or required.

Although a process may be described singly or without reference to other products or methods, in an embodiment the process may interact with other products or methods. For example, such interaction may include linking one business model to another business model. Such interaction may be provided to enhance the flexibility or desirability of the process.

Although a product may be described as including a plurality of components, aspects, qualities, characteristics and/or features, that does not indicate that any or all of the plurality are preferred, essential or required. Various other embodiments within the scope of the described invention(s) include other products that omit some or all of the described plurality.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a PDA" does not imply that any or all of the three items of that list are mutually exclusive and does not imply that any or all of the three items of that list are comprehensive of any category.

An enumerated list of items (which may or may not be numbered) does not imply that any or all of the items are equivalent to each other or readily substituted for each other.

All embodiments are illustrative, and do not imply that the invention or any embodiments were made or performed, as the case may be.

V. Computing

It will be readily apparent to one of ordinary skill in the art that the various processes described herein may be implemented by, e.g., appropriately programmed general purpose computers, special purpose computers and computing devices. Typically a processor (e.g., one or more microprocessors, one or more microcontrollers, one or more digital signal processors) will receive instructions (e.g., from a memory or like device), and execute those instructions, thereby performing one or more processes defined by those instructions. Instructions may be embodied in, e.g., one or more computer programs, one or more scripts.

A "processor" means one or more microprocessors, central processing units (CPUs), computing devices, microcontrollers, digital signal processors, or like devices or any combination thereof, regardless of the architecture (e.g., chip-level multiprocessing/multi-core, RISC, CISC, Microprocessor without Interlocked Pipeline Stages, pipelining configuration, simultaneous multithreading).

Thus a description of a process is likewise a description of an apparatus for performing the process. The apparatus that performs the process can include, e.g., a processor and those input devices and output devices that are appropriate to perform the process.

Further, programs that implement such methods (as well as other types of data) may be stored and transmitted using a variety of media (e.g., computer readable media) in a number of manners. In some embodiments, hard-wired circuitry or custom hardware may be used in place of, or in combination with, some or all of the software instructions that can implement the processes of various embodiments. Thus, various combinations of hardware and software may be used instead of software only.

The term "computer-readable medium" refers to any medium, a plurality of the same, or a combination of different media, that participate in providing data (e.g., instructions, data structures) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read.

Various forms of computer readable media may be involved in carrying data (e.g. sequences of instructions) to a processor. For example, data may be (i) delivered from RAM to a processor; (ii) carried over a wireless transmission medium; (iii) formatted and/or transmitted according to numerous formats, standards or protocols, such as Ethernet (or IEEE 802.3), SAP, ATP, Bluetooth☐, and TCP/IP, TDMA, CDMA, and 3G; and/or (iv) encrypted to ensure privacy or prevent fraud in any of a variety of ways well known in the art.

Thus a description of a process is likewise a description of a computer-readable medium storing a program for performing the process. The computer-readable medium can store (in any appropriate format) those program elements which are appropriate to perform the method.

Just as the description of various steps in a process does not indicate that all the described steps are required, embodiments of an apparatus include a computer/computing device operable to perform some (but not necessarily all) of the described process.

Likewise, just as the description of various steps in a process does not indicate that all the described steps are required, embodiments of a computer-readable medium storing a program or data structure include a computer-readable medium storing a program that, when executed, can cause a processor to perform some (but not necessarily all) of the described process.

Where databases are described, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats (including relational databases, object-based models and/or distributed databases) could be used to store and manipulate the data types described herein. Likewise, object methods or behaviors of a database can be used to implement various processes, such as the described herein. In addition, the databases may, in a known manner, be stored locally or remotely from a device which accesses data in such a database.

Various embodiments can be configured to work in a network environment including a computer that is in communication (e.g., via a communications network) with one or more devices. The computer may communicate with the devices directly or indirectly, via any wired or wireless medium (e.g. the Internet, LAN, WAN or Ethernet, Token Ring, a telephone line, a cable line, a radio channel, an optical communications line, commercial on-line service providers, bulletin board systems, a satellite communications link, a combination of any of the above). Each of the devices may themselves comprise computers or other computing devices, such as those based on the Intel® Pentium® or Centrino™ processor, that are adapted to communicate with the computer. Any number and type of devices may be in communication with the computer.

In an embodiment, a server computer or centralized authority may not be necessary or desirable. For example, the present invention may, in an embodiment, be practiced on one or more devices without a central authority. In such an embodiment, any functions described herein as performed by the server computer or data described as stored on the server computer may instead be performed by or stored on one or more such devices.

Where a process is described, in an embodiment the process may operate without any user intervention. In another embodiment, the process includes some human intervention (e.g., a step is performed by or with the assistance of a human).

VI. Continuing Applications

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application.

Applicants intend to file additional applications to pursue patents for subject matter that has been disclosed and enabled but not claimed in the present application.

VII. 35 U.S.C. § 112, Paragraph 6

In a claim, a limitation of the claim which includes the phrase "means for" or the phrase "step for" means that 35 U.S.C. § 112, paragraph 6, applies to that limitation.

In a claim, a limitation of the claim which does not include the phrase "means for" or the phrase "step for" means that 35 U.S.C. § 112, paragraph 6 does not apply to that limitation, regardless of whether that limitation recites a function without recitation of structure, material or acts for performing that function. For example, in a claim, the mere use of the phrase "step of" or the phrase "steps of" in referring to one or more steps of the claim or of another claim does not mean that 35 U.S.C. § 112, paragraph 6, applies to that step(s).

With respect to a means or a step for performing a specified function in accordance with 35 U.S.C. § 112, paragraph 6, the corresponding structure, material or acts described in the specification, and equivalents thereof, may perform additional functions as well as the specified function.

Computers, processors, computing devices and like products are structures that can perform a wide variety of functions. Such products can be operable to perform a specified function by executing one or more programs, such as a program stored in a memory device of that product or in a memory device which that product accesses. Unless expressly specified otherwise, such a program need not be based on any particular algorithm, such as any particular algorithm that might be disclosed in the present application. It is well known to one of ordinary skill in the art that a specified function may be implemented via different algorithms, and any of a number of different algorithms would be a mere design choice for carrying out the specified function.

Therefore, with respect to a means or a step for performing a specified function in accordance with 35 U.S.C. § 112, paragraph 6, structure corresponding to a specified function includes any product programmed to perform the specified function. Such structure includes programmed products which perform the function, regardless of whether such product is programmed with (i) a disclosed algorithm for performing the function, (ii) an algorithm that is similar to a disclosed algorithm, or (iii) a different algorithm for performing the function.

Where there is recited a means for performing a function that is a method, one structure for performing this method includes a computing device (e.g., a general purpose computer) that is programmed and/or configured with appropriate hardware to perform that function. Also includes a computing device (e.g., a general purpose computer) that is programmed and/or configured with appropriate hardware to perform that function via other algorithms as would be understood by one of ordinary skill in the art.

VIII. Disclaimer

Numerous references to a particular embodiment does not indicate a disclaimer or disavowal of additional, different embodiments, and similarly references to the description of embodiments which all include a particular feature does not indicate a disclaimer or disavowal of embodiments which do not include that particular feature. A clear disclaimer or disavowal in the present application shall be prefaced by the phrase "does not include" or by the phrase "cannot perform".

IX. Incorporation By Reference

Any patent, patent application or other document referred to herein is incorporated by reference into this patent application as part of the present disclosure, but only for purposes of written description in accordance with 35 U.S.C. § 112, paragraph 1 and enablement in accordance with 35 U.S.C. § 112, paragraph 1, and should in no way be used to limit, define, or otherwise construe any term of the present application where the present application, without such incorporation by reference, would not have failed to provide an ascertainable meaning, but rather would have allowed an ascertainable meaning for such term to be provided. Thus, the person of ordinary skill in the art need not have been in any way limited by any embodiments provided in the reference Any incorporation by reference does not, in and of itself, imply any endorsement of, ratification of or acquiescence in any statements, opinions, arguments or characterizations contained in any incorporated patent, patent application or other document, unless explicitly specified otherwise in this patent application.

X. Prosecution History

In interpreting the present application (which includes the claims), one of ordinary skill in the art shall refer to the prosecution history of the present application, but not to the prosecution history of any other patent or patent application, regardless of whether there are other patent applications that are considered related to the present application, and regardless of whether there are other patent applications that share a claim of priority with the present application.

Embodiments

In various embodiments, a bet is available that pays off if a group of horses finish a race in a particular order. For example, with horses 1, 2, 3, 4, 5, 6, 7, and 8, the bet may pay off only if horses finish with #8 in first place, #7 in second, #6 in third, #5 in fourth, #4 in fifth, #3 in sixth, #2 in seventh, and #1 in eighth. In some embodiments, the bet pays off only if all horses in a race finish in an order most contrary to common expectation. For example, the bet pays off if the favorite horse (the horse providing the lowest payout per dollar wagered in a pari-mutuel environment) finishes last, the next most favored horse finishes second to last, the third most favored horse finishes third to last, and so on, with the biggest underdog finishing first. In such embodiments, the bet may be termed a "reverse bet". Since a reverse bet often pays only in the case of a very unlikely event, the amount paid may be quite large. The possibility for a large payout may be an appealing reason for horse racing fans to place bets. Although reference herein will often be made to horse racing, it should be understood that a reverse bet may be available with dog racing, car racing, or any other applicable contest.

Terminology

Payoff odds: the amount that will be paid per unit wager should a given event occur (e.g., a given horse winning a race). Payoff odds may be written as "x:y" indicating that x units are paid per y units wagered. Note that the wager is also returned to the bettor. Payoff odds may be normalized to be written as "z:1", indicating that z units are paid per unit wagered. Equivalently, normalized payoff odds may be simply written as "z". In general, payoff odds for an event are greater the more unlikely the event, and vice versa. Thus, for example, a favored horse in a race will have lower payoff odds than a long-shot horse.

Reverse bet: a bet which pays off if all horses (or other contenders) in a race finish in an order most contrary to common expectation (e.g., as indicated by payoff odds in a pari-mutuel system).

Determining Which are the Favored Horses

The determination of the horse most favored to win, the horse next most favored to win, and so on may occur:

- Based on the payoff odds in a pari-mutuel system. The horse with the lowest payoff odds may be determined to be the favorite, the horse with the next lowest payoff odds may be determined to be the $2^{nd}$ most favored horse, and so on.
- By vote or decision of a group of racing fans or enthusiasts.
- By vote or decision of one or more experts in the field, such as professional gamblers, bookmakers, sports journalists, etc.
- Using certain algorithms applied to historical data about the horses, race track, jockeys, trainers, race style, etc.

Computing the Probability of a Reverse Bet Winning

In various embodiments, the probability of a horse winning a race is derived from the payoff odds for the horse. In a pari-mutuel embodiment, let W represent the amount of money in the win pool for a race, which includes all monies that people have bet on various horses in the race to win. Let $w_1, w_2, w_3 \ldots$ represent the amount of money people have bet on horse 1, horse 2, horse 3, etc., to win. Note that $W=w_1+w_2+w_3+\ldots$ . Let t represent the take percent, or the percentage of money that will be removed from the win pool for taxes, fees, track profits, and so on. What remains to be distributed to people who bet on the winning horse is thus $W*(1-t)$. If horse k wins, then the people who bet on horse k receive $W*(1-t)$ after having put in $w_k$, providing them payoff odds of $W*(1-t)/w_k$. Let $p_1, p_2, p_3$, etc. represent the probabilities that horses 1, 2, 3, etc. will win. These probabilities are not necessarily known, but may be implied if one assumes: 1) bettors wish to place wagers even if such wagers provide expectations of loss; 2) given that bettors do wish to place wagers, bettors wish to maximize their expected winnings per dollar wagered; 3) bettors all agree on the probability that each horse will win; 4) bettors can place wagers of infinitely small amounts; and 5) bettors can bet as often as they want. The expected winnings per dollar wagered from a bet on horse k is given by $p_k*W*(1-t)/w_k$. If the expected winnings for horse k are greater than for any other horse, it is anticipated that bettors would start placing additional bets on horse k. This would have the effect of increasing both $w_k$ and W, though $w_k$ would increase by a greater percentage. Thus, the expected winnings for horse k per dollar wagered would decrease, while the increase in W would drive up expected winnings for other horses. In this way, expected winnings for all horses would tend to equalize. It has been shown above that $W*(1-t)$ is distributed for every W wagered. Thus, if the expected winnings over all horses is the same, expected winnings are $W*(1-t)/W$, or $1-t$ per dollar wagered. Thus we have $p_k*W*(1-t)/w_k=(1-t)$, or $p_k=w_k/W$. Thus, the probability of a horse winning can be derived as the amount of wagers place on that horse to win divided by the total amount of wagers placed on any horse to win.

In various embodiments, the probability of a horse winning (or of finishing in any other place) may be derived using other algorithms, such as statistical algorithms or neural networks which predict a horse's performance based on a number of inputs. Such inputs may include the horse's age, performance history, days of rest, favored courses, trainer, jockey, lineage, gender, weight, health history, position in the starting gate, and so on. In various embodiments, the probability of a horse winning (or finishing in any other place) may be determined by an expert in the field, such as a sports journalist.

Once probabilities $p_1, p_2, p_3$, etc., have been obtained for each horse to win, additional assumptions can be made in order to derive the probability of a horse finishing second, third, etc., given a different horse finishes first. In some embodiments, it is assumed that out of a given group of horses, regardless of any other events that may occur, the probability of horse n finishing in place q given that horse m finished in place q–1 is equal to the a-priori probability that horse n finishes in place q–1 divided by one minus the probability that horse m finishes in place q–1. For example, the probability that horse 3 finishes second given that horse 5 finishes first is equal to $p_3/(1-p_5)$.

With the above assumptions the probability that the reverse bet wins can be derived. Assume in an N-horse race, $p_1 > p_2 > p_3 > \ldots > p_N$ so that the reverse bet pays off if horse 1 finishes last, horse 2 finishes second to last, and so on, with horse N finishing first. Now, the probability of horse N finishing first is $p_N$. The probability of horse N–1 finishing second given that horse N finished first is $p_{N-1}/(1-p_N)$. The probability of horse N–2 finishing third given that horse N finished first and horse N–1 finished second is:

$$(p_{N-2}/(1-p_N))/(1-p_{N-1}/(1-p_N)) =$$
$$(p_{N-2}/(1-p_N))/((1-p_N-p_{N-1})/(1-p_N)) = p_{N-2}/(1-p_N-p_{N-1})$$

The probability of horse N–3 finishing fourth given that horse N finished first, horse N–1 finished second, and horse N–2 finished third is:

$$p_{N-3}/(1-p_N-p_{N-1})/(1-p_{N-2}/(1-p_N-p_{N-1})) =$$
$$p_{N-3}/(1-p_N-p_{N-1})/((1-p_N-p_{N-1}-p_{N-2})/(1-p_N-p_{N-1})) =$$
$$p_{N-3}/(1-p_N-p_{N-1}-p_{N-2})$$

The probability for all the horses finishing in reverse order is thus given by:

$$\Pi_{k=1 \ldots N} p_k / \Pi_{k=1 \ldots N-1}(1 - \Sigma_{j=1 \ldots k} p_{N-j+1})$$

A simple example is as follows. Suppose there are four horses in a race. $400 is bet on horse 1, $300 on horse 2, $200 on horse 3, and $100 on horse 4. Thus, $w_1=\$400$, $w_2=\$300$, $w_3=\$200$, $w_4=\$100$. The amount of money put into the win pool, W, is thus $1000. The probability of horse 1 winning can be derived as $p_1=w_1/W=\$400/\$1000=0.4$. Similarly, $p_2=\$300/\$1000=0.3$, $p_3=\$200/\$1000=0.2$, $p_4=\$100/\$1000=0.1$.

The probability of all four horses finishing in reverse order is:

$$p_1 * p_2 * p_3 * p_4 / ((1-p_4)*(1-p_3-p_4)*(1-p_2-p_3-p_4)) =$$
$$0.4 * 0.3 * 0.2 * 0.1 / ((1-0.1)*(1-0.2-0.1)*$$
$$(1-0.3-0.2-0.1)) = 0.0095$$

It will be appreciated that this probability is significantly lower than if all four horses were considered roughly equal contenders. If all horses were equal, the probability of a given order of horses would be $\frac{1}{4}*\frac{1}{3}*\frac{1}{2}=0.042$.

It should also be appreciated that the above formula for the probability of a finish in reverse order is based on one set of assumptions, and does not necessarily hold under alternate sets of assumptions.

One set of assumptions can be used to compute the probabilities of the k least favored horses finishing in the first k places in reverse order to the order that would be expected. For example, the probability of horses N and N−1 finishing first and second, respectively, in a race can be computed as: $p_N * p_{N-1}/(1-p_N)$. Following the finishes in the first k places, it may then be assumed that all orders of finish for places k+1 through N are equally likely. This assumption might be based on the belief, for example, that horses do not try hard in a race anymore once it is clear they will not finish in the first k places. For example, only the first k places may award a purse. Thus, the probability of any particular order of finishes in places k+1 through N, given that particular horses finish in places 1 through k is $1/((N-k)!)$. Modifying the 4-horse example above, the probability for horse 4 to finish first and horse 3 to finish second is:

$$p_4 * p_3/(1 - p_4) = 0.1 * 0.2/(1 - 0.1) = .022$$

Given that horse 4 finishes first and horse 3 finishes second, the probability that horse 2 will finish third and horse 1 will finish fourth is now assumed to be $1/((4-2)!) = 1/2$. Thus, the probability for all four horses finishing in reverse order would be: $0.022 * 1/2 = 0.011$.

Betting Structure

Pari-Mutuel

In some embodiments, bettors may choose any order of finish for the horses in a race. Bettors place a bet on their chosen order. All money that has been bet by any bettor on a particular order of finish is then placed into a pool. A percentage of the pool may then be taken out for taxes, track profits, and so on. The remainder of the pool may then be paid to a bettor if his chosen order of finish transpires in the actual race. For example, suppose a bettor bets that horse 3 will finish first, horse 1 will finish second, horse 2 will finish third, horse 4 will finish fourth, horse 5 will finish fifth, horse 6 will finish sixth, horse 7 will finish seventh, and horse 8 will finish eighth. If the outcome of the race proves the bettor to be correct in his choice, then the bettor will be paid the entire pool of bets (less any amount taken out) on the horses in a race all finishing in a particular order. If two or more bettors have placed bets on a particular winning order, then the two or more bettors may share the pool in proportion to the bet amounts placed on the winning order.

In some embodiments, if no better has bet on exactly the order of finish that has come to pass, then the winning bettor may be the one who has matched the most places correctly. For example, suppose six of eight horses have finished in exactly the places predicted by a bettor, but two of eight have not. If no other bettor has matched six places, then the bettor having matched six places will win the pool of bets (less take outs). If several bettors have matched six places then, in some embodiments, all may share the pool in proportion to the amounts bet. In some embodiments, among multiple bettors making a partial match, the winning bettor may be the one who has correctly predicted the earliest places. For instance, a bettor who has correctly predicted the horses finishing first through sixth may win over a bettor who has correctly predicted the horses finishing third through eighth.

In some embodiments, if no bettor has correctly predicted the entire order of finish in a race, then the pool of bets may not be awarded. Rather, the pool may be kept by the track, carried over to the next race, donated to charity, or put to some other use.

Fixed Odds

A race track, casino, bookmaker, or other establishment may offer fixed payoff odds on a reverse bet. For example, a race track may offer payoff odds of 100,000:1 on a reverse bet. In various embodiments, fixed odds may be offered for any bet that selects all horses to finish in a particular order.

Fixed Pool

A race track, casino, bookmaker, or other establishment may offer a fixed pool to be paid out in the event that a reverse bet wins. For example, a $1,000,000 pool is offered. The pool is then divided among all winning bettors. Note that in various embodiments, with a fixed pool, a bettor's payout is dependent upon bets made by other bettors, whereas with fixed odds, the bettor's payout is not.

Growing Pool

A pool may be offered that grows for every race in which a reverse bet does not win. For example, suppose in a first race that $1000 worth of bets are placed on a reverse bet. If the reverse bet wins, then the pool (less take outs) may be divided among the winners. However, if the reverse bet does not win, then a portion of the pool (e.g., 75% after take outs) may be carried over to a second race. Suppose that $500 is carried over to the second race and that $2000 worth of bets are placed on the second race. Of the $2000, suppose that $400 are removed for taxes, track profits, and so on. There is then $2100 available for payout in the second race, including the $500 carried over from the first race, and the $1600 derived from new bets on the second race. If there is no winner in the second race, then a portion of the $2100 may be carried over to a third race, and so on.

Carry-Over of Wagers in a Pool

As described above, when there is no winner of a reverse bet (or of some other bet where a particular order of finish is required) for a first race, then a portion of bets placed may be awarded to a winning bettor in a subsequent race. Thus, there may be a growing pool of money available to be awarded for so long as there is no winner of a reverse bet.

- In some embodiments, 100% of the amount available to be paid out in a first race is carried over to a second race should there be no winner of a reverse bet in the first race. Note that the 100% available to be paid out may include the total amount of bets placed less any amounts taken out.
- In some embodiments, less than 100% is carried over to a second race. The money not carried over may be kept by the track, donated to charity, paid as a consolation prize for anyone who has correctly chosen e.g., the horses that would finish in at least 6 of the places, etc. Exemplary percentages to be carried over are 75%, 50%, and (66+2/3)%.
- In some embodiments, a pool of money to be paid out for a winning reverse bet may be applicable only to certain races. A pool may be applicable to:
- Races run only on a particular track
- Races run only in a particular geographic region, such as a state
- Races run only during a particular time period, such as during a particular day
- In some embodiments, a pool of money to be paid out for a winning reverse bet may grow based on money bet on reverse bets at tracks throughout a region, throughout a country, or throughout the entire world. With contributions to the pool coming from many tracks, the pool may grow quite large in a short period of time. Such a large pool might provide an exciting experience for bettors placing reverse bets.

Ties and Pool Division

In some embodiments, it is foreseeable that, should a reverse bet win, there would be multiple winners. In the event of multiple winners:

- The amount to be paid out may be allocated to all the winners in proportion to the amounts bet by the winners.
- There may be a drawing or lottery among the winners to determine who will receive the entire pool. In the drawing, each of the winners may receive tickets or other chances to win which are based on the amount wagered on the reverse bet. For example, each winner may receive a number of tickets in a drawing equal to the number of dollars wagered on the reverse bet.
- There may be no awarding of the pool.
- The pool may be awarded based on some kind of play-off among the winners. For example, the winner who makes the most accurate prediction for one or more future races may take the entire pool.

Choosing the Bet

In some embodiments, there is only a single order of finish, e.g., an order of finish in reverse of common expectation, that is available. In such embodiments, a bettor may simply indicated whether or not he wishes to bet on this order of finish.

In some embodiments the order of finish required in a reverse bet is based on the payoff odds after the close of betting.

In some embodiments, the order of finish required in a reverse bet is based on the payoff odds at the moment the reverse bet is placed.

In some embodiments, an order of finish is randomly selected for a bettor, e.g., using a random number generator. The bettor then places his bet on this order of finish. The order of finish may be chosen before or after the bettor makes his bet. If before, the bettor may have the choice of making the bet or not.

In some embodiments, the bettor may select an order of finish. The bettor may fill out a card where a series of identifiers is listed for all horses in a race. For instance, the names of all the horses in a race are listed. The bettor may then indicate, for each horse, an expected place, such as first place, second place, etc. The bettor may make his indication by filling in one of a set of numbered bubbles. The bettor may make his indication by writing in a place number. In some embodiments, the places are listed (e.g., first place through eighth place), and next to each placed the bettor indicates the identifier of a particular horse.

A bettor may place a bet and/or select an order of finish using a physical substrate, such as a paper betting slip, using an electronic interface at a self-service betting machine, using a GUI for betting over the Internet, using a phone touchpad for bets placed over the phone, or in any other manner.

Availability of Reverse Bet

- The bet may only be available if there are at least x number of horses in a race. As will be appreciated, the likelihood of the reverse bet winning may be quite high if there are only a small number of horses in a race.
- The bet may only be available if certain information is already commonly known about one or more horses.
  - The horse(s) has competed before
  - The horse(s) is of a known lineage (e.g., descendent from known race horses)
  - The jockey(ies) has competed before
  - The horse has been tested for drugs
- The bet may be available only in certain tracks, such as tracks that are considered in a certain tier, have been around a certain length of time, have established a good reputation, are in a certain location, etc.

Preventing Cheating and Manipulation

It is possible that the payoff odds for a horse winning a race might be manipulated in such a way that the payoff odds do not accurately represent the true probability of the horse winning the race. For example, in a pari-mutuel system, a person might place a very large wager on a horse even though the horse is known to be an insignificant contender. Such a wager might artificially alter the payoff odds for the horse such that the horse becomes the favorite. In this way, the person can increase the likelihood that horses in the race will finish in an order opposite that which would be expected from examination of the payoff odds. Thus, various embodiments may discourage manipulation of the odds. In some embodiments, a reverse bet may not be available or not honored if:

- The probabilities for horses finishing in various places as derived from the payoff odds are significantly divergent from the probabilities set forth by one or more human experts or computer algorithms. For example, if the probability of any horse winning, as calculated from the payoff odds, is more than 0.1 away from the probability set forth by an expert, the reverse bet may not be honored.
- The total amount bet on individual horses to win is less than a predetermined amount, e.g., $10,000.
- The total number of bettors is less than a predetermined number, e.g., 500.
- More than a predetermined percent of the amounts bet on horses to win is accounted for by less than a predetermined number of people. For example, if more than 20% of the amounts bet on horses to win were placed by less than 10 people, then the reverse bet may not be honored.
- More than a predetermined percent of the number of bets placed on horses to win is accounted for by less than a predetermined number of people.

The following is a list of embodiments, not claims.

Applicants claim:

A. An apparatus comprising a computing device operable to:

- receive a first set of bets for a first horse to win a race (e.g., 12 different people may place a bet such that if the first horse wins, the 12 people will win money from those who have bet on other horses to win);
- receive a second set of bets for a second horse to win the race;
- determine, based on the first set of bets and the second set of bets, an order in which the first and second horses might finish the race;
- receive from a bettor a third bet for the order to transpire;
- determine actual results of the race; and
- pay the bettor an amount which is based on the third bet, the order, and the actual results of the race.

The order in which the first and second horses might finish the race is merely a possibility of what might happen. As such the possibility need not be realistic, likely, or need not actually ever happen. In various embodiments, the order determined may be an order where the horse for which the most amount of money has been bet to win finishes last, and the horse for which the lease amount of money has been bet to win finishes first. Thus, the determined order may actually represent an order of finish that is least likely to occur. Once the order has been determined, the bettor may make the third bet that the order itself will happen. Thus, the third bettor may place the third bet not on any one particular horse, but on an order in which a plurality of horses will finish. Once the actual results of the race of been determined (e.g., once the race has been run), the third bettor may be paid.

B. The apparatus of embodiment A in which to receive a second set of bets includes to receive a second set of bets that total to less than the total of the first set of bets.

C. The apparatus of embodiment B in which to determine an order includes to determine, based on the first set of bets and the second set of bets, that the second horse will finish the race before the first horse.

D. The apparatus of embodiment A in which to pay the bettor includes to pay the bettor a positive amount which is based on the third bet if the actual results of the race match the order.

E. An apparatus comprising a computing device operable to:
  determine a number of participants in a race;
  determine if the number of participants exceeds a predetermined threshold;
  receive, for each participant in the race, at least one bet that the participant will win the race;
  determine, based on the received bets, a potential order for the participants to finish the race;
  offer, if the number of participants exceeds the predetermined threshold, a fixed prize pool for any bet that is successfully made that the potential order will transpire;
  receive a first bet from a first bettor that the potential order will transpire;
  determine an actual order of the race;
  determine whether the actual order matches the potential order; and
  provide at least a portion of the fixed prize pool to the first bettor.

The fixed prize pool may represent a fixed amount of money. The same amount of money may be offered for every race meeting certain conditions, such as races having more participants than the predetermined threshold. The fixed prize pool may be 1 million dollars, for example. The fixed prize pool may not vary even though the number of bets on races may vary.

F. The apparatus of embodiment E in which to determine a number of participants in a race includes to determine a number of horses in a race.

G. The apparatus of embodiment E in which to determine a number of participants in a race includes to determine a number of one of: (a) horses, (b) dogs, (c) cars, (d) camels, (e) sail boats, (f) people, (g) runners, (h) cyclists, (i) swimmers, (j) boats, and (k) computer generated characters.

H. The apparatus of embodiment E in which the computing device is further operable to cause to be displayed an indication of the size of the fixed prize pool. For example, the computing device may instruct a public monitor or display to show "$1,000,000" or any other indication of the size of the fixed prize pool.

I. The apparatus of embodiment E in which to offer includes to offer, if the number of participants exceeds the predetermined threshold, one million dollars to be divided among all bettors who successfully bet that the order will transpire.

J. The apparatus of embodiment E in which to determine a potential order includes to determine, based on the received bets, a potential order in which it is least likely that the participants will finish the race. For example, the potential order may have the horse on which the least amount was wagered finishing first, the horse on which the next least amount was wagered finishing second, and so on.

K. The apparatus of embodiment J in which to determine a potential order includes to determine an order such that the lower the total of bets placed on a given participant, the earlier the given participant will finish the race.

L. The apparatus of embodiment E in which the computing device is further operable to cause to be displayed an indication of the potential order. The apparatus may cause to be displayed on a public monitor the potential order.

M. The apparatus of embodiment L in which to cause to be displayed an indication of the potential order includes to cause to be displayed in indication that a first participant will finish first, that a second participant will finish second, that a third participant will finish third, that a fourth participant will finish fourth, that a fifth participant will finish fifth, that a sixth participant will finish sixth, that a seventh participant will finish seventh, that an eighth participant will finish eighth, that a ninth participant will finish ninth, that a tenth participant will finish tenth, that an eleventh participant will finish eleventh, and that a twelfth participant will finish twelfth.

N. The apparatus of embodiment E in which to provide at least a portion of the fixed prize pool to the first bettor includes to:
  determine a number of bettors that had bet that the potential order would transpire;
  divide the fixed prize pool by the number of bettors, thereby to generate a number of substantially equal portions of the fixed prize pool; and
  provide to the first bettor one of the number of portions.

Thus, for example, if four bettors had bet on the potential order, the fixed prize pool may be divided into four equal portions. Thus, for example, a $1 million prize pool may be divided into four equal portions of $250,000. Each of the four bettors may receive $250,000.

O. The apparatus of embodiment E in which to determine if the number of participants exceeds a predetermined threshold includes to determine if the number of participants exceeds seven.

P. An apparatus comprising a computing device operable to:
  receive, for each participant in a race, at least one bet that the participant will win the race;
  determine, based on the received bets that the respective participants will win the race, a first potential order for the participants to finish the race;
  receive from a first bettor, after determining a first potential order, a first bet that the first potential order will transpire;
  receive for a particular participant in the race, after receiving the first bet, an additional bet that the particular participant will win the race;
  determine, based on the additional bet, a second potential order for the participants to finish the race;
  determine an actual order in which the participants finished the race; and
  provide payment to the first bettor based on the actual order and at least one of the first potential order and the second potential order.

The first potential order above may be determined such that the horse with the least amount bet on it to win is to finish first, the horse with the next least amount bet on it to win is to finish second, and so on. However, once the additional bet is placed, a first horse that had less bet on it to win as compared with a second horse, may now have more bet on it to win than does the second horse. Thus, a second potential order may be determined where the first and second horses have switched places as compared to the first potential order.

Q. The apparatus of embodiment P in which to provide payment includes to provide payment to the first bettor if the actual order matches the first potential order.

In some embodiments, after a first bettor makes a bet on a first potential order, his bet remains on that same first potential order, even though subsequent bets on various horses to win may mean that the first potential order is no longer deemed the least likely to transpire.

R. The apparatus of embodiment P in which to provide payment includes to provide payment to the first bettor if the actual order matches the second potential order.

In some embodiments, the first bettor bets on the order of finish that will be deemed least likely following the close of betting. Thus, even if currently the first potential order is deemed the least likely, the second potential order may be the order that is deemed least likely at the close of betting, such as after subsequent bets have been placed on other horses. The bet made by the first bettor may then win only if the second potential order actually transpires.

S. The apparatus of embodiment P in which to determine a second potential order includes to determine, based on the additional bet, a second potential order for the participants to finish the race, in which the second potential order is different from the first potential order.

T. The apparatus of embodiment P in which to determine a second potential order includes to determine, based on the additional bet, a second potential order for the participants to finish the race, in which the particular participant finishes in a worse position in the second potential order than the particular participant finishes in the first potential order.

The invention claimed is:

1. A scale comprising
    a plurality of weight sensors;
    a communications port;
    a display device;
    at least one processor to:
        detect a plurality of weight readings from the plurality of weight sensors, each weight sensor being arranged to accommodate a foot of a horse;
        compare the plurality of weight readings;
        identify whether a pair of the weight readings diverge by more than a predetermined threshold;
        render on the display device an indication of an injury of the horse, if the pair of the weight readings diverge by more than a predetermined threshold; and
        transmit, via the communication port, the indication of the injury to a server enabled to compute horse racing odds based at least partially on the injury indication.

2. The scale of claim 1, wherein a given weight sensor is configured to transmit a weight reading to the at least one processor periodically.

3. The scale of claim 2, wherein the at least one processor is further configured to compute an average of weight readings received periodically from the given weight sensor.

4. The scale of claim 1, wherein a given weight sensor is configured to transmit a weight reading to the at least one processor every sixty seconds.

5. The scale of claim 1, wherein the predetermine threshold is ten percent.

6. The scale of claim 1, wherein the at least one processor is configured to render weight determinations and a percentage of difference between the weight determinations on the display device.

7. The scale of claim 1, wherein a weight reading from a given weight sensor is a function of time.

8. A method comprising
    detecting, by at least one processor, a plurality of weight readings from a plurality of weight sensors, each weight sensor being arranged to accommodate a foot of a horse;
    comparing, by the at least one processor, the plurality of weight readings;
    identifying, by the at least one processor, whether a pair of the weight readings diverge by more than a predetermined threshold;
    rendering, by the at least one processor, an indication of an injury of the horse on a display device, if the pair of the weight readings diverge by more than a predetermined threshold; and
    transmitting, by the at least one processor, the indication of the injury to a server enabled to compute horse racing odds based at least partially on the injury indication.

9. The method of claim 8, further comprising receiving, by the at least one processor, a weight reading from a given weight sensor periodically.

10. The method of claim 8, further comprising computing, by the at least one processor, an average of weight readings received periodically from a given weight sensor.

11. The method of claim 8, further comprising receiving, by the at least one processor, a weight reading from a given weight sensor every sixty seconds.

12. The method of claim 8, wherein the predetermine threshold is ten percent.

13. The method of claim 8, further comprising rendering, by the at least one processor, weight determinations and a percentage of difference between the weight determinations on the display device.

14. The method of claim 8, wherein a weight reading from s given weight sensor is a function of time.

* * * * *